Figure 1:
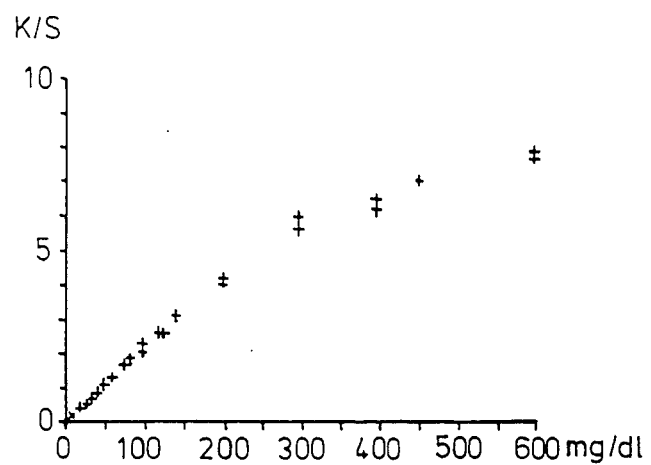

United States Patent [19]

Bömer et al.

[11] Patent Number: 4,800,169

[45] Date of Patent: Jan. 24, 1989

[54] TEST AIDS AND METHOD FOR THE PREPARATION THEREOF

[75] Inventors: Bruno Bömer, Berg.-Gladbach; Karl-Erwin Piejko, Cologne, both of Fed. Rep. of Germany

[73] Assignee: Miles Inc., Elkart, Ind.

[21] Appl. No.: 74,238

[22] Filed: Jul. 16, 1987

[30] Foreign Application Priority Data

Jul. 31, 1986 [DE] Fed. Rep. of Germany ....... 3625852

[51] Int. Cl.⁴ .................. G01N 21/03; C12Q 1/28
[52] U.S. Cl. ..................... 436/166; 436/170; 422/68; 435/28
[58] Field of Search ............ 435/904, 27, 28; 436/166, 164, 138, 136, 135, 127, 74, 66

[56] References Cited

U.S. PATENT DOCUMENTS

| Re. 30,267 | 5/1980 | Bruschi | 436/170 |
| 4,089,747 | 5/1978 | Bruschi | 436/95 |
| 4,184,923 | 1/1980 | Schubert | 435/28 |
| 4,460,684 | 7/1984 | Bauer | 435/28 |

FOREIGN PATENT DOCUMENTS 3422732 10/1985 Fed. Rep. of Germany .

*Primary Examiner*—Sidney Marantz
*Assistant Examiner*—Lyle Alfandary-Alexander
*Attorney, Agent, or Firm*—Roger N. Coe

[57] ABSTRACT

A process for preparing test aids for detecting substances to be analyzed by means of redox reactions containing single component oxidation indicators as the indicator substance in which oxidizable aromatic amine or hydrazino compounds, which are not capable of coupling with themselves, are added as decolorants.

6 Claims, 1 Drawing Sheet

TEST AIDS AND METHOD FOR THE PREPARATION THEREOF

The present invention relates to a method for the preparation of test aids for detecting substances to be analyzed by means of redox reactions in which a single-component indicator is used as the indicator substance and, in addition, in which oxidizable aromatic amino or hydrazinol compounds, which are not capable of coupling with themselves, are added to the test aid as decolorants.

The addition of the decolorant prevents the appearance of a blank color value of the test aid. The addition of relatively large quantities of the decolorant makes it possible to adjust the sensitivity of the test aid precisely.

In recent years, the so-called "color tests" have acquired ever-increasing importance in medical diagnostics. The "color tests" are methods for detecting substances to be analyzed in which peroxides such as, hydrogen peroxide or cumene hydroperoxide play a part. Hydrogen peroxide is produced during the oxidation, catalyzed by suitable oxidases, of a substance to be analyzed in the presence of oxygen. In these color tests either liquid reagents or so-called test strips are used as test aids. Possible substances to be analyzed are glucose, glycerol, glycerol phosphate, sarcosine, galactose and cholesterol. As appropriate oxidases, mention can be made of glucose oxidase, glycerol oxidase, glycerol phosphate oxidase, sarcosine oxidase, galactose oxidase and cholesterol oxidase. Still other enzyme/substrate pairs are known in addition.

The cumene hydroperoxide mentioned above is employed to detect substances which are peroxidatively active, such as hemoglobin. The detection of concealed blood in stool samples is based on this principle.

All these detection methods have in common the fact that redox equivalents, catalyzed by peroxidase or a peroxidatively active substance, are transferred from the peroxide to an indicator. These indicators can be divided into two groups.

1. Single-component indicators.

In these indicators the redox equivalents are transferred to an indicator and the resultant oxidation product is colored. As typical representatives mention can be made of benzidine, alkylbenzidines, such as tetramethyl-, tetraethylbenzidine or tolidine, etc.

2. Two-component indicators.

In these indicators one component is oxidized by the transfer of the redox equivalents. This colorless oxidation product is capable of reacting with a suitable coupling component to form a dyestuff. Probably the most well known reaction of this type is the so-called "Trinder reaction" [Trinder, P.A., *Ann. Clin. Biochem.*, 6:24-27 (1969)]in which 4-aminoantipyrine is the oxidizable component which reacts with a phenol as coupling component to form a red quinone imine dyestuff. In a similar system 3-methyl-2-benzothizolinonehydrazone finds application as the oxidizable component.

The advantage of detection methods which proceed via peroxide is their high sensitivity which makes it possible to detect extremely small quantities of a substance to be analyzed. The high sensitivity, however, also results in a high susceptibility to interference. Thus, before the sample to be analyzed is added, the indicators mentioned produce distinct colorations even with traces of oxidatively active impurities or with atmospheric oxygen during the preparation of test strips or when liquid analyses are being carried out. This has the result that before a quantitative analysis is carried out a blank has to be measured which has to be subtracted from the measured value after the analysis. In particular, low concentrations of substances to be analyzed can only be determined imprecisely. To avoid these blank values, it would be possible, in principle, to work only with highly purified reagents with atmospheric oxygen being excluded, but this cannot be implemented technically because of the high costs.

In DE-OS (German Published Specification) No. 2,716,060 stabilized rapid methods of diagnosis are described employing oxidation indicators to which aryl semicarbazides are added to avoid the appearance of a blank color value. These aryl semicarbazides must, however, be added in large quantities [Examples are described in the DE-OS (German Published Specifications) No. 3,012,368 and No. 3,406,328]and are, in addition, suspected of being carcinogenic, so that their use in test aids is inadvisable.

Attempts to avoid the blank color value of test aids by adding ascorbic acid resulted in irreproducible results in relation to the sensitivity of the test aid if the ascorbic acid was added in quantities sufficient for the above-mentioned purpose.

It has now been found that reagents, reagent solutions or impregnating solutions for preparing test aids which contain single-component oxidation indicators can be decolored or the formation of a blank color value can be prevented by adding small quantities oxidizable aromatic amino or hydrazino compounds, which do not couple with themselves, as decolorants.

It has further been found that a reduction of the sensitivity and a shift in the calibration relationship (intensity of coloration as a function of the concentration of the substance to be analyzed) towards higher concentrations of the substance to be analyzed can be achieved by adding larger quantities of the decolorants.

The invention relates to a process for preparing test aids for detecting substances to be analyzed by means of redox reactions containing single-component oxidation indicators as the indicator substance in which oxidizable aromatic amino or hydrazino compounds, which are not capable of coupling with themselves, are added as decolorants.

The decolorants are employed for decoloring the test aid in concentrations of between 0.05 and 5% by weight referred to the single-component oxidation indicator and preferably between 0.1 and 1% by weight. The appropriate quantity can readily be determined by titrating the impurities. A small excess does not have a measurable affect on the calibration relationship.

In order to reduce the sensitivity of the test aid or to shift the intersection of the calibration curve with the abscissa towards higher concentrations, the decolorants are used in quantities of between 5 and 200% by weight, preferably between 5 and 100% by weight, of the oxidation indicator.

The invention further relates to a method for preparing a colorless impregnating solution or reagent mixtures which serve to prepare test strips and contain the single-component oxidation indicators, said solutions or mixtures additionally containing the decolorants.

The invention further relates to test aids containing single-component oxidation indicators and, additionally, the decolorants. Test aids are understood to mean reagent mixtures, lyophilization products, reagent combinations, liquid reagents, etc.

In addition, the invention relates to the use of the test aids for detecting substances to be analyzed. Suitable substances to be analyzed are glucose, cholesterol, triglycerides, galactose, etc. or enzymes such as peroxidase or proteins with peroxidative activity such as hemoglobin or methemoglobin.

As possible sample materials mention can be made of body fluids such as blood, plasma, liquor, urine and stool samples.

The decolorants to be used according to the invention are normally employed as oxidizable components in two-component indicator systems, but within the framework of the present invention are used without any coupling component.

Suitable decolorants are, for example, 4-aminopyrazolinones substituted in the 3 position of the general formula

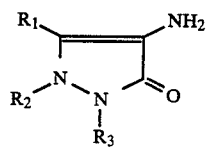

where
$R_1 = C_1-C_4$ alkyl, optionally substituted by —OH, OR, OCOR, OCOOR, $C_1-C_4$ alkoxy, aryl, aralkyl, R representing $C_1-C_4$ alkyl,
$R_2 = H$, $C_1-C_4$ alkyl,
$R_3 = $ aryl, aralkyl, $C_1-C_4$ alkyl, optionally substituted as in the case of $R_1$, H, or 2-benzothiazolinone hydrazones of the general formula

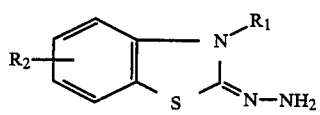

where
$R_1 = H$, $C_1-C_4$ alkyl,
$R_2 = H$, $SO_3H$.

4-aminoantipyrine (formula I, $R_1 = R_2 =$ methyl, $R_3 =$ phenyl) or 3-methyl-2-benzothiazolinone hydrazone (formula II, $R_1 =$ methyl, $R_2 =$ H) are preferred.

EXAMPLE 1

To prepare a glucose test film the following mixture is prepared:
9 mg of glucose oxidase (250 U/mg),
50 mg peroxidase (80 U/mg) and
1 mg 4-aminoantipyrine dissolved in
1.7 ml of citrate buffer (1 m, pH 5.5).
This solution is dispersed in the form of fine droplets in
3.4 ml of chloroform which contains
0.34 g of Na dodecylbenzensulphonate
by shaking. The dispersion produced is added to a mixture of 16 ml of a w/o dispersion with chloroform as the oil phase, a w/o ratio of 1:1 and 13.1% by weight of polyacrylamide [preparation described in DE-OS (German Published Specification) No. 3,434,822, Example 8] and 34 ml of a 7.5% solution of cellulose acetobutyrate $[n_{rel}](19\%$ in acetone: ethanol=19:1)=200]in chloroform and 0.6 g of 3,3', 5,5'-tetramethylbenzidine. The mix is vigorously shaken. During this process a strong green coloration of the mix first appears, which disappears again, however, after 30–90 seconds.

The mix is deposited by means of a doctor blade on polyester film (180 μm wet coating) and dried by blowing with warm air at 24° C. in the dark. A white test film is obtained which is cut into strips 0.5 cm wide.

For testing, 30 μl of complete blood is applied to a test area with a size of 0.5 cm × 1 cm and wiped off after 15 seconds. The color which forms in accordance with the glucose content of the blood sample is measured in a reflection photometer at 640 nm and the K/S value $[K/S=(1-R)^2/2R;$ where R=reflection, K=adsorption coefficient and S=scattered light coefficient]is calculated. The plot of K/S against the glucose concentration (calibration curve) determined by means of above test strips is shown in FIG. 1. It can be seen that the curve has a K/S value of zero at the concentration zero. The coloration produced by a blood sample containing 20 mg/dl glucose can be distinguished visually from the color of the untested strip.

COMPARISON EXAMPLE 1

If the procedure is as in Example 1, but without 4-aminoantipyrine being added, a green colored mixture and a bright green colored test strip are obtained. A calibration curve drawn up by means of these test strips has a K/S value different from zero at a glucose concentration of zero. The coloration produced by a blood sample containing 20 mg/dl of glucose cannot be distinguished visually from the blank color value of the test strip.

EXAMPLE 2

Figure 2:
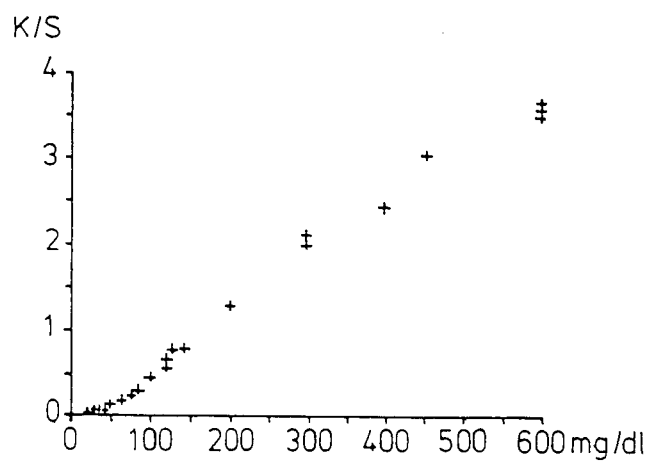

A mixture is prepared according to Example 1, but using 2.6 ml of citrate buffer which contains a total of 100 mg of 4-aminoantipyrine in addition to the enzymes. The test strip prepared with this mixture as in Example 1 is tested with blood samples of various glucose concentrations as in Example 1. The calibration curve obtained in this process is shown in FIG. 2. A shift of the abscissa intersection to approximately 30 mg/dl glucose and a substantially lower slope of the calibration curve between 30 and 200 mg/dl glucose in comparison to FIG. 1, i.e., a lower sensitivity, can be seen.

EXAMPLE 3

A mixture is prepared according to Example 1, but using 2 mg of 3-methyl-2-benzothiazolinone hydrazone hydrochloride instead of 4-aminoantipyrine. As in Example 1, a coloration of the initially green mixture is observed. The test strips prepared by means of this mixture yield the same calibration curve as the test strips from Example 1 (FIG. 1).

Obviously, many modifications and variations of the invention as hereinbefore set forth can be made without departing from the spirit and scope thereof and therefore only such limitations should be imposed as are indicated by the appended claims.

What is claimed is:

1. A method for preparing a test aid for detecting an analytical substance by means of a redox reaction which method comprises adding a decolorant consisting essentially of an oxidizable aromatic amino or hydrazino compound which does not couple with itself to a single-component indicator composition devoid of any coupling component capable of reacting with an oxidation product to form a dyestuff.

2. The method according to claim 1 in which the decolorant is added in a concentration between 0.05 and 5 percent by weight based on said indicator.

3. The method according to claim 1 in which the decolorant is added in a concentration between 5 and 200 percent by weight based on said indicator.

4. A composition for use in a redox reaction for detecting an analytical substanace, said composition comprising a single-component indicator composition devoid of any coupling component capable of reacting with an oxidation product to form a dyestuff together with a decolorant consisting essentially of an oxidizable aromatic amino or hydrazino compound which does not couple with itself.

5. The composition of claim 4 in which the decolorant is 3-methyl-2-benzothiazolinone.

6. The composition of claim 4 in which the decolorant is 4-aminoantipyrine.

* * * * *